United States Patent [19]
Ward

[11] 4,217,461
[45] Aug. 12, 1980

[54] OLEFINIC HYDROCARBON ISOMERIZATION PROCESS

[75] Inventor: Dennis J. Ward, South Barrington, Ill.

[73] Assignee: UOP Inc., Des Plaines, Ill.

[21] Appl. No.: 60,714

[22] Filed: Jul. 26, 1979

[51] Int. Cl.² .................. C07C 5/24; C07C 11/02
[52] U.S. Cl. ............................ 585/668; 585/664; 585/670; 585/800
[58] Field of Search .................. 585/664, 668, 670

[56] References Cited

U.S. PATENT DOCUMENTS

| | | |
|---|---|---|
| 2,421,229 | 5/1947 | Zimmerman ................ 585/668 |
| 3,290,404 | 12/1966 | Howman et al. ............. 585/668 |
| 3,821,123 | 6/1974 | Germanas et al. ........... 585/668 |
| 4,104,321 | 8/1978 | Ward .......................... 585/668 |

Primary Examiner—Veronica O'Keefe
Attorney, Agent, or Firm—James R. Hoatson, Jr.; John F. Spears, Jr.; William H. Page, II

[57] ABSTRACT

A process for the isomerization of normal olefinic hydrocarbons is disclosed. The feed stream is passed through a first reaction zone and is then cooled sufficiently to cause the condensation of from about 1 to 25 mole percent of the hydrocarbons in the isomerization zone effluent stream. The uncondensed portion of the effluent of the first reaction zone is heated and passed through a second reaction zone which is maintained at a lower temperature than the first reaction zone. The product isomer is recovered from the effluent of the second reaction zone.

8 Claims, 1 Drawing Figure

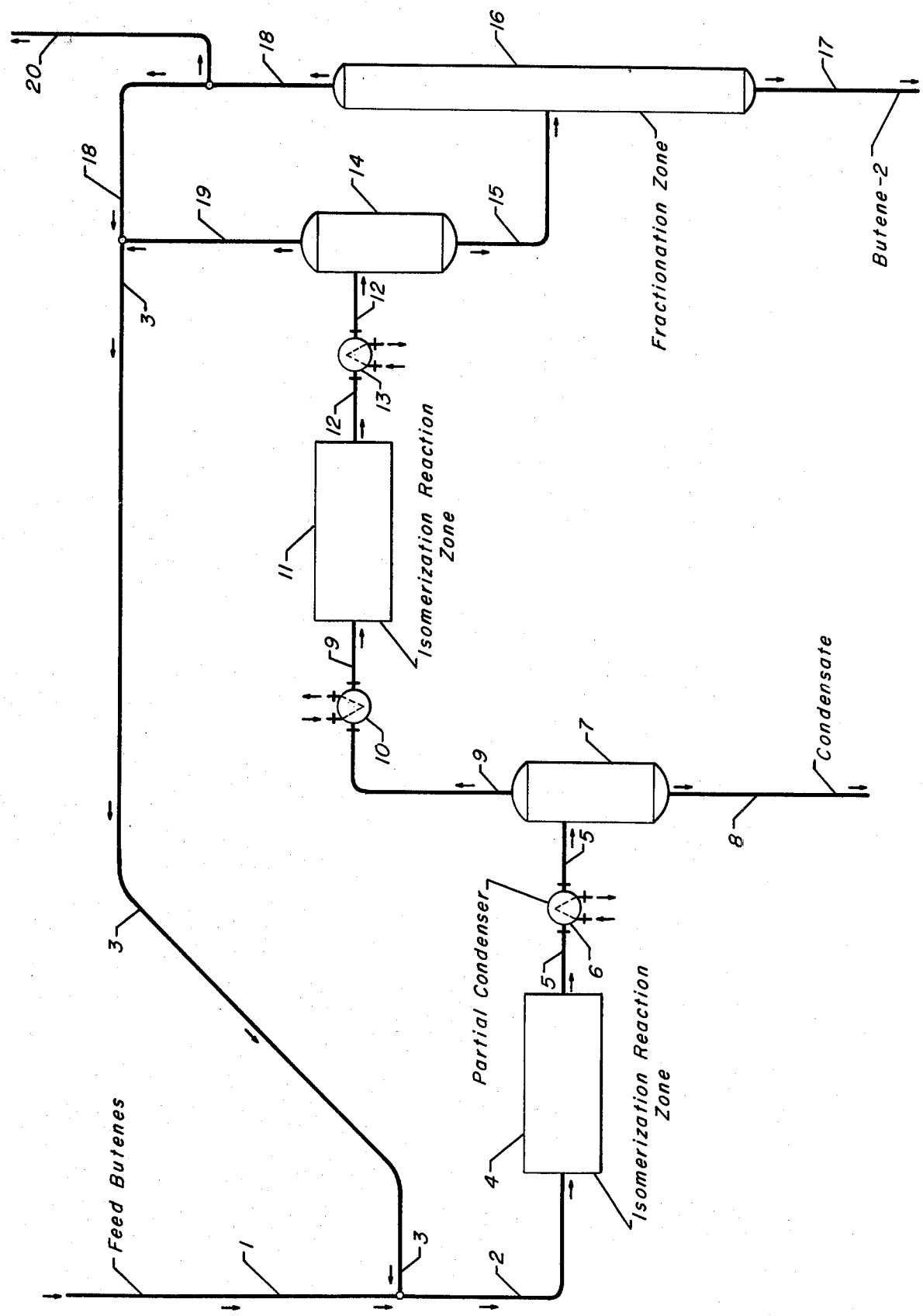

OLEFINIC HYDROCARBON ISOMERIZATION PROCESS

FIELD OF THE INVENTION

The invention relates to a hydrocarbon conversion process. The invention more specifically relates to a process for the isomerization of hydrocarbons. The invention is specifically directed to a process for the isomerization of normal olefinic hydrocarbons having from four to seven carbon atoms per molecule. The invention therefore relates to processes similar in nature to those found in Classes 260 and 208.

PRIOR ART

The isomerization of normal olefinic hydrocarbons is described in U.S. Pat. No. 3,821,123 (Cl. 252–439) issued to Germanas and Pollitzer. This reference describes a catalyst which may be used in the isomerization of butene-1 to butene-2. The reference also discusses an isomerization process utilizing the catalyst and includes a description of the olefinic hydrocarbons which may be processed and suitable reaction conditions.

U.S. Pat. No. 4,104,321 (Cl. 260–677A) issued to D. J. Ward discloses a process for the separation of olefinic hydrocarbons which utilizes two olefin isomerization reaction zones. However, in this process the two isomerization reaction zones are not operated in series and independently derived feed streams are passed into each of the isomerization reaction zones.

It is believed that heretofore the condensation and removal of a portion of the hydrocarbon content of a process stream flowing through two isomerization reaction zones has not been practiced. Rather, it is believed that either the entire effluent of the first isomerization reaction zone was passed into the second isomerization reaction zone or that the effluent of the first isomerization reaction zone was passed into a separatory zone wherein the product isomer was preferentially removed.

BRIEF SUMMARY OF THE INVENTION

The invention provides a novel and improved process for the isomerization of normal olefinic hydrocarbons. The invention is based on the observation that sulfur compounds, which are strong catalyst inhibitors and thus cause a high temperature requirement in an isomerization zone, react with olefinic hydrocarbons in the isomerization zone to form high boiling compounds. In the subject process selective condensation of a small portion of the effluent of a first isomerization reaction zone effects the removal of the majority of these high boiling compounds from the effluent stream of the first isomerization reaction zone. The remaining uncondensed hydrocarbons and hydrogen is then heated to a temperature somewhat lower than that employed in the first isomerization reaction zone. The heated vapor stream is then passed through a second isomerization reaction zone, resulting in a much higher conversion than could be achieved in a single stage isomerization process operated at the higher temperature of the first isomerization reaction zone.

One embodiment of the invention may be characterized as a process for the isomerization of normal olefinic hydrocarbons which comprises the steps of passing a first feed stream which comprises a first normal olefinic hydrocarbon through a first isomerization reaction zone operated at isomerization conditions which include a first temperature to form a first isomerization reaction zone effluent stream comprising a second normal olefinic hydrocarbon; condensing between about 1.0 and 25 mole percent of the first isomerization reaction zone effluent stream to thereby form a second feed stream and a condensate stream which is removed from the process; passing the second feed stream through a second isomerization reaction zone operated at conditions which include a lower second temperature to form a second isomerization reaction zone effluent stream; and recovering the second normal olefinic hydrocarbon.

BRIEF DESCRIPTION OF THE DRAWING

The Drawing illustrates one embodiment of the invention. For purposes of simplicity and ease of understanding many pieces of apparatus which are required for the successful operation of the process, such as pumps, compressors, temperature, pressure, and flow rate monitoring and control systems, reboilers and flow control valves, etc., have not been shown. This representation of one embodiment is not intended to preclude from the scope of the inventive concept those other embodiments disclosed herein or which result from the reasonable and expected modifications which may be made by those skilled in the art.

Referring now to the Drawing, a feed stream comprising butene-1 enters the process through line 1. A recycle stream carried by line 3 is admixed with the feed stream and the feed stream is then passed into a first isomerization reaction zone 4 through line 2. This isomerization reaction zone is operated at conditions which effect the conversion of butene-1 to butene-2. The effluent stream of the first isomerization reaction zone is carried by line 5 through a condenser 6 wherein it is partially condensed and is then transferred to a vapor-liquid separation zone 7. A relatively small condensate stream which preferably contains less than 10 mole percent of the hydrocarbons in the effluent of the first isomerization reaction zone is removed from the process in line 8. The majority of the hydrocarbons in the effluent of the first isomerization reaction zone are not condensed and are removed from the vapor-liquid separation zone 7 through line 9.

The vapor stream flowing through line 9 is heated by indirect heat exchange in a heater 10 and is then passed into a second isomerization reaction zone 11 as the feed stream to this zone. This isomerization reaction zone is also maintained at conditions which effect the conversion of butene-1 to butene-2, but is operated at a lower average temperature than the first isomerization reaction zone. The effluent stream of the second isomerization reaction zone is carried by line 12 through a condenser 13 and is directed into a second vapor-liquid separation zone 14. A vapor stream which comprises the majority of the hydrogen which enters zone 14 is removed in line 19 as a recycle gas stream.

Substantially all the hydrocarbons present in the effluent stream of the second isomerization reaction zone are removed from the vapor-liquid separation zone 14 as a liquid phase hydrocarbon stream carried by line 15 and passed into a fractionation zone 16. This fractionation zone is operated at conditions effective to produce a net overhead stream which contains at least a majority of the butene-1 which is present in the liquid-phase hydrocarbon stream. This net overhead stream is recycled to the first isomerization reaction zone through lines 18 and 3. a net bottoms stream comprising the product butene-2 is removed from the fractionation zone through line 17. A drag stream comprising isobutylene and butene-1 may be removed from the process through line 20 to prevent the buildup within the process of isobutylene present in the feed stream.

DETAILED DESCRIPTION

It is becoming a normal occurrence for a chemical or petrochemical process to consume only one specific olefinic hydrocarbon isomer. For instance, it may be desired to charge a high purity stream of butene-1 or isobutylene to a process as one of the feedstocks. It is often the case with many olefinic hydrocarbons that the amount of a specific olefinic hydrocarbon available from its normal source of supply is not in balance with the demand for this one specific hydrocarbon. In these instances the ability to isomerize olefinic hydrocarbons fulfills the very useful purpose of converting the available excess isomers into those for which a greater demand exists. The isomerization of olefinic hydrocarbons also finds utility as a part of a process for the separation or purification of isomeric hydrocarbons.

It is an objective of the subject invention to provide an improved process for the isomerization of olefinic hydrocarbons. A further objective of the present invention is to provide a process for the isomerization of normal olefinic hydrocarbons having four or five carbon atoms per molecule. The specific objective of the invention is to provide a high conversion process for the isomerization of butene-1 to butene-2.

The traditional major source of light olefins has been as by-products of the fluidized catalytic cracking (FCC) process which is utilized as a basic unit in a great many oil refineries. Butenes are also produced as by-products in cracking processes designed to produce ethylene and propylene as a main product. Another source of butenes and other olefins is the dehydrogenation of the corresponding paraffinic hydrocarbon.

Butene-2 is consumed in the production of several chemicals which are widely used or are themselves consumed in other chemical products including various plastics and solvents. some of the more widely used chemicals produced from butene-2 are sec butyl alcohol, maleic anhydride, butadiene and methyl ethyl ketone.

The subject process provides a method of increasing the conversion which is achieved in a single pass of a feed stream through an isomerization zone. This ability to produce higher conversions is beneficial in that it may reduce the required size of the isomerization zone reactors or reduce the size and operating costs of product separation facilities. Other benefits such as lower overall operating expenses or higher purity products may also accrue through use of the process.

The basic flow of the subject process comprises the passage of the feed hydrocarbon in admixture with hydrogen through a first isomerization reaction zone, the cooling and partial condensation of the effluent of the first isomerization reaction zone effluent to effect the separation of at least the majority of the high boiling compounds from this effluent stream, and the passage of the uncondensed portion of the effluent into a second isomerization reaction zone operated at a lower temperature. There is no separation performed between the first and the second isomerization reaction zone other than a phase separation employed to remove the condensate. The condensate may be removed from the process, passed into the fractionation zone in which the product is recovered or passed into the vapor-liquid separator which receives the effluent of the second isomerization reaction zone. It is preferred that the condensate is passed into the fractionation zone to allow the recovery of cocondensed olefins.

The basis for this partial condensation and separation step is the observation that sulfur compounds, which are strong catalyst inhibitors and thus cause a high temperature requirement, react with the olefins within the reaction zone to form high boiling compounds thought to be thioethers. By condensing a small portion of the effluent of a first reaction zone, the high boiling sulfur compounds are effectively removed from the remaining vapor. This vapor may then be processed in a second reaction zone at a lower temperature because of the absence of the deleterious high boiling compounds. This increases the overall conversion which may be achieved. The subject process is thereby capable of lowering any 50% the butene-1 concentration in the isomerate as compared to a conventional single reaction zone system for the isomerization of butene.

Between 1.0 and 25.0 mole percent of the hydrocarbons contained in the effluent of the first isomerization reaction zone may be condensed in the partial hydrocarbon condensation step of the process. However, it is greatly preferred that only the minimum condensation necessary to remove the desired portion of the high boiling compounds is performed within this step. As some of the olefinic hydrocarbons will also be condensed, the maximum desired amount of total condensation may be expressed in terms of the amount of hydrocarbons which are condensed. It is preferred that less than 10.0 mole percent of the total hydrocarbons are condensed. To ensure the removal of the high boiling catalyst deactivating compounds at least about 4.0 mole percent of the hydrocarbons should be condensed. The high boiling sulfur-containing compounds are not considered as hydrocarbons in determining the percentage condensation at this point in the process.

This intermediate partial condensation step is to be distinguished from the conventional near-total hydrocarbon condensation which is performed on the effluent of the second isomerization reaction zone. The near-total condensation step is performed to allow the facile separation of the olefinic hydrocarbons from the hydrogen which is to be recycled. It is this near-total condensation which is similar to that performed in prior art porcesses and which produces a liquid-phase hydrocarbon stream containing at least 75 mole percent of the total hydrocarbons in the isomerization reaction zone effluent stream.

After the intermediate partial condensation the remaining vapors are heated and passed into a second isomerization reaction zone. This zone is operated at an average temperature which is from about 30° C. to about 120° C. lower than that which is maintained in the first isomerization reaction zone. The lower temperature is beneficial in allowing a closer approach to the maximum theoretical conversion. Isomerization conditions include a temperature within the broad range of about 45° C. to about 250° C. Both isomerization reaction zones are operated within this range. The range of preferred temperatures is from 75° C. to 160° C. The first and the second isomerization reaction zones are preferably operated at substantially the same pressure. This pressure may range from subatmospheric to about 30 atmospheres or more. The pressure maintained in the second isomerization reaction zone will normally be somewhat lower than that in the first due to the inherent pressure drop through the interconnecting conduits and the two heat exchangers needed for the partial condensation and vapor reheating steps. The pressure difference between the two isomerization reaction zones is preferably less than 1.0 atmosphere.

The preferred catalyst is one which contains sulfided nickel supported on a refractory inorganic base similar to the isomerization catalyst described in U.S. Pat. No. 3,821,123. Other catalysts may be employed in the subject process if desired. Both the first and the second isomerization reaction zones preferably comprise a single fixed bed reactor through which the reactants flow in a downward direction. Other types of reactors including moving bed reactors and radial flow reactors may also be used if so desired. The reactant stream which is passed into the first isomerization reaction zone will preferably contain over 0.1 mole of hydrogen for each mole of hydrocarbon in the feed stream. Less than 1.0 mole of hydrogen per mole of hydrocarbon is desirable.

The space velocity and the temperature maintained within an isomerization reaction zone is normally balanced with the activity of the catalyst and the composition of the feed stream to give high conversions at relatively high space velocities. An olefin liquid hourly space velocity (liquid volume of $C_4$ and heavier olefins per hour per unit volume of catalyst employed) of between 0.5 and 20 may be maintained. This space velocity is calculated based on the total catalyst located in both isomerization reaction zones. An olefin liquid hourly space velocity between 1.0 and 10.0 is preferred At lower space velocities, a lower temperature may normally be employed.

The subject process may be employed in the isomerization of any isomerizable hydrocarbon which is benefited by the ability to operate the reaction zones at a lower average temperature. It is specifically beneficial in the isomerization of normal olefinic hydrocarbons. Olefinic hydrocarbons having less than eight carbon atoms per molecule are the preferred feed hydrocarbons. The pentenes and butenes are especially preferred feed hydrocarbons. The application of the process to higher carbon number olefins is limited only by processing problems in the vaporization, separation and purification of higher molecular weight olefins.

In accordance with this description the invention may be characterized as a process for the isomerization of normal olefinic hydrocarbons which comprises the steps of passing a first vapor-phase feed stream which comprises a first normal olefinic hydrocarbon through a first isomerization reaction zone operated at isomerization conditions which include a first temperature and thereby forming a first isomerization reaction zone effluent stream comprising the first normal olefinic hydrocarbon and a second normal olefinic hydrocarbon which is an isomer of the first normal olefinic hydrocarbon; condensing between about 1.0 and 25 mole percent of the hydrocarbons contained in the first isomerization reaction zone effluent stream and thereby forming a liquid-phase condensate stream and a second vapor-phase feed stream; passing the second vapor-phase feed stream through a second isomerization reaction zone operated at isomerization conditions which include a lower second temperature and thereby forming a second isomerization reaction zone effluent stream; and recovering the second normal olefinic hydrocarbon as a product.

The overall flow scheme employed in utilizing the inventive concept will be dependent on such variables as the composition of the feed stream and the desired product composition. For instance, if the feed steam contained only butene-1, it would not be necessary to remove any other major stream other than a product stream comprising butene-2. However, if the feed stream contains isobutane and/or isobutylene in addition to butene-1, then these additional compounds would be concentrated in the unconverted butene. This would necessitate either further separation procedures which are not shown in the Drawing or the removal of a drag stream containing these compounds. The adaptation of the inventive concept to these various required flow schemes is believed to be within the expertise of those skilled in the art of hydrocarbon processing.

The heat exchange required in heating the two feed streams and in cooling the effluent of the first isomerization reaction zone lends itself to many possible process design variation. Again, those skilled in process design are capable of selecting heat exchange systems and flow paths which are cost-effective in minimizing the utilities costs of heating and cooling within the process. The feedeffluent heat exchange normally employed in hydrocarbon conversion processes and the recovery of heat for use within the fractionation zone are both contemplated. The fractionation zone in which the product isomer is recovered will preferably comprise one or more trayed fractionation columns. The separation of light olefins in this zone is an ideal situation for the use of a heat pump system to minimize utilities cost. The separation of light olefins by fractionation is described in U.S. Pats. Nos. 3,013,952; 3,568,457 and 4,137,129.

I claim as my invention:

1. In a process for the isomerization of olefinic hydrocarbons having less than eight carbon atoms per molecule wherein a vapor-phase feed stream comprising a first olefinic hydrocarbon and hydrogen is passed through an isomerization reaction zone containing an isomerization catalyst in which zone portion of the first olefinic hydrocarbon is transformed into an isomer of the first olefinic hydrocarbon; a vapor-phase isomerization reaction zone effluent stream is partially condensed to form a recycle gas stream and a liquid-phase hydrocarbon stream containing at least 75 mole percent of the total hydrocarbons in the vapor-phase isomerization zone effluent stream; and the isomer of the first olefinic hydrocarbon is recovered from the liquid-phase hydrocarbon stream as a product; the improvement which comprises:

(a) partially condensing the vapor-phase effluent stream of a first isomerization reaction zone which is operated at a first temperature and then separating a resultant liquid-phase condensate stream which contains less than 25 mole percent of the total hydrocarbons in the vapor-phase effluent stream of the first catalytic isomerization rection zone from the remaining uncondensed portion of the vapor-phase effluent stream of the first catalytic isomerization reaction zone;

(b) heating the remaining uncondensed portion of the vapor-phase effluent stream of the first catalytic isomerization reaction zone;

(c) passing the remaining uncondensed portion of the vapor-phase effluent stream of the first catalytic isomerization reaction zone through a second catalytic isomerization reaction zone operated at a lower second temperature; and, (d) partially condensing the vapor-phase effluent stream of the second catalytic isomerization reaction zone to thereby form the liquid-phase hydrocarbon stream and the recycle gas stream.

2. The improvement of claim 1 further characterized in that the first olefinic hydrocarbon has four or five carbon atoms per molecule.

3. The improvement of claim 1 further characterized in that the first olefinic hydrocarbon is butene-1.

4. A process for the isomerization of normal olefinic hydrocarbons which comprises the steps of:
  (a) passing a first vapor-phase feed stream which comprises a first normal olefinic hydrocarbon through a first catalytic isomerization reaction zone operated at isomerization conditions which include a first temperature and thereby forming a first catalytic isomerization reaction zone effluent stream comprising the first normal olefinic hydrocarbon and a second normal olefinic hydrocarbon which is an isomer of the first normal olefinic hydrocarbon;
  (b) condensing between about 1.0 and 25 mole percent of the hydrocarbons contained in the first catalytic isomerization reaction zone effluent stream and thereby forming a liquid-phase condensate stream and a second vapor-phase feed stream;
  (c) passing the second vapor-phase feed stream through a second catalytic isomerization reaction zone operated at isomerization conditions which include a lower second temperature and thereby forming a second catalytic isomerization reaction zone effluent stream comprising the second normal olefinic hydrocarbon; and,
  (d) recovering the second normal olefinic hydrocarbon.

5. The process of claim 4 further characterized in that the first normal olefinic hydrocarbon has four or five carbon atoms per molecule.

6. The process of claim 4 further characterized in that the first normal olefinic hydrocarbon is butene-1.

7. The process of claim 6 further characterized in that between about 4.0 and 10.0 mole percent of the first catalytic isomerization reaction zone effluent stream is condensed.

8. The process of claim 7 further characterized in that the lower second temperature is from about 30 to 120° C. lower than the first temperature.

* * * * *